United States Patent
Nan et al.

(10) Patent No.: US 11,331,413 B1
(45) Date of Patent: May 17, 2022

(54) PREPARATION METHOD AND APPLICATION OF COMPOSITE SCAFFOLD FOR DIRECTIONALLY GUIDING REGENERATION OF OPTIC NERVE AXONS

(71) Applicant: WENZHOU MEDICAL UNIVERSITY, Wenzhou (CN)

(72) Inventors: Kaihui Nan, Wenzhou (CN); Tonghe Pan, Wenzhou (CN); Yangjun Chen, Wenzhou (CN); Jingjie Wang, Wenzhou (CN); Sen Lin, Wenzhou (CN); Lingli Li, Wenzhou (CN)

(73) Assignee: Wenzhou Medical University, Wenzhou (CN)

( * ) Notice: Subject to any disclaimer, the term of this patent is extended or adjusted under 35 U.S.C. 154(b) by 0 days.

(21) Appl. No.: 17/413,492

(22) PCT Filed: Sep. 18, 2020

(86) PCT No.: PCT/CN2020/116163
§ 371 (c)(1),
(2) Date: Jun. 11, 2021

(87) PCT Pub. No.: WO2022/052150
PCT Pub. Date: Mar. 17, 2022

(30) Foreign Application Priority Data

Sep. 10, 2020 (CN) .......................... 202010944499.7

(51) Int. Cl.
A61L 27/26 (2006.01)
A61L 27/50 (2006.01)

(52) U.S. Cl.
CPC ............... *A61L 27/26* (2013.01); *A61L 27/50* (2013.01); *A61L 2430/32* (2013.01)

(58) Field of Classification Search
None
See application file for complete search history.

(56) References Cited

FOREIGN PATENT DOCUMENTS

| CN | 102671237 A | 9/2012 |
| CN | 106729983 A | 5/2017 |
| CN | 208860768 U | 5/2019 |

*Primary Examiner* — Hasan S Ahmed
*Assistant Examiner* — Randeep Singh
(74) *Attorney, Agent, or Firm* — Christensen, Fonder, Dardi & Herbert PLLC

(57) ABSTRACT

A preparation method and an application of a composite scaffold for directionally guiding regeneration of optic nerve axons. A major component of the composite scaffold is prepared from one or more degradable biomedical materials combined according to different ratios by a gradient freezing method. To increase a mechanical property of the scaffold or prolong in-vivo degradation time, the scaffold may be cross-linked by a biological cross-linker. After a gelatin is added, the prepared composite scaffold exhibits excellent mechanical properties and biocompatibility. A problem of solubility differences of the gelatin A produced during gradient freezing can be regulated by sodium alginate, thereby facilitating regular directional pipeline morphology of the scaffold. After cross-linked with genipin, the composite scaffold significantly enhances stability, and the directional pipeline morphology of the scaffold cam provide attachment sites for regeneration of the optic nerve axons, thereby guiding directional regeneration of the optic nerve axons.

5 Claims, 9 Drawing Sheets

After cross-linking

| | Genipin cross-linking | Glutaraldehyde cross-linking | EDC+NHs cross-linking |
|---|---|---|---|
| Expansion rate | 31.3%±10.6% | 74.1%±29.7% | 82.2%±41.4% |
| Moisture content | 91.4%±0.5% | 91.0%±0.5% | 91.5%±1.4% |
| Swelling ratio | 10.7±0.7 | 10.1±0.6 | 11.1±2.1 |

PREPARATION METHOD AND APPLICATION OF COMPOSITE SCAFFOLD FOR DIRECTIONALLY GUIDING REGENERATION OF OPTIC NERVE AXONS

RELATED APPLICATIONS

The present application is a National Phase entry of PCT Application No. PCT/CN2020/116163, filed Sep. 18, 2020, which claims priority to Chinese Patent Application No. 2020109444997, filed Sep. 10, 2020, the disclosures of which are hereby incorporated by reference herein in their entirety.

FIELD OF THE INVENTION

The present invention relates to the technical field of optic nerve repair scaffolds, and more particularly relates to a preparation method and an application of a composite scaffold for directionally guiding regeneration of optic nerve axons.

BACKGROUND OF THE INVENTION

Bodies of retinal ganglion cells (RGCs) are located inside optic nerves; and axons of the RGCs are projected to eyeballs so as to converge into the optic nerves. The optic nerves of each eye are composed of about 1.2 million RGC axons, and have ophthalmic artery branch infusion. Impairment of the optic nerves is collectively called optic neuropathy, and may be caused by glaucoma, traumaticopticneuropathy (TON) and various ischemic, genetic and neurogenic diseases. TON is one of the complications of craniocerebral injury, and refers to simultaneous optic nerve injuries of facial, craniocerebral, orbital or posterior ocular injuries due to various external force causes and may have no external or initial injuries of the eyeballs or optic nerves under an ophthalmoscope after injury, but may still cause visual deterioration or visual field defect at different degrees, and even total loss of vision. Treatment principles of TON mainly include protection of the injured optic nerves to avoid apoptosis and promotion of regeneration and functional reconstruction of the optic nerve axons. Limiting factors of optic nerve regeneration may be divided into internal factors and external factors. The internal factors are mainly as follows: 1, apoptosis of the RGCs caused by optic nerve injuries will up-regulate downstream factors of apoptosis-related signaling pathways (P53 and Bax) and increase oxidative stress levels of the RGCs, thereby further facilitating apoptosis of the RGCs; and 2, during differentiation and maturation of the RGCs, intracellular programs of the RGCs are transformed to proliferation inhibition. Reports show that, signaling pathways, such as cAMP, mTOR/PTEN and KLF4, in many cells may induce transcription cascade or epigenetic alterations, and these alterations are closely related to maturity of a central nervous system. Therefore, regeneration difficulty of axons of the RGCs after the optic nerve injuries may be related to regulation of these molecules. The external factors mainly include deficiency of a neurotrophic factor, glial scar at an injured end and myelin. The myelin is a lipoprotein produced from glial cells and has effects of insulating and accelerating electrical conduction. Existence of the myelin is regarded as a reason that the central nervous system has poorer regeneration capacity than a peripheral nervous system. For example, Vajda F et al., have reported that, a myelin-associated protein (Nogo) that is highly expressed on oligodendrocyte of the central nervous system is a major inhibitor of axon regeneration of the central nervous system. In addition, other myelin-associated proteins such as semaphorin 4D, myelin-associated glycoprotein (MAG), oligodendrocyte-associated glycoprotein (OMgp) and tyrosine protein kinase B3 (ephrin B3) are proved to be associated with inhibition of growth of the axons. Meanwhile, after the central nervous system is injured, myelin removal efficiency is lowered; myelin is easily accumulated in an external environment; and a myelin product can limit regeneration of the axons and activate apoptosis cascade, thereby further promoting neuronal apoptosis. After the optic nerves are injured, retinal glia cells including oligodendrocyte, astrocyte and retinal microglial cells are activated; multiple axon growth inhibition factors are up-regulated; and chondroitin sulfate, protein polysaccharides and reactive astrocyte are promoted to form the glial scar. The glial scar is an unsuitable environment for regeneration of the optic nerve axons, and is also a mechanical barrier for growth of the optic nerve axons. Study suggests that, decrease of the glial scar may promote regeneration of the optic nerve axons.

With respect to the above factors, much research work has been done in China and abroad, and mainly includes the following aspects: 1, proliferation inhibition of the intracellular programs is opened on a genetic level in gene therapy modes such as adeno-associated virus (AAV), thereby promoting regeneration of the optic nerve axons; 2, a difficulty that the neurotrophic factor lacks after the optic nerve are injured is improved by providing an exogenous neurotrophic factor, thereby promoting regeneration of the axons; 3, due to application of anti-inflammatory and anti-apoptotic drugs, apoptosis of the RGCs caused by inflammations and oxidative stress after injuries is decreased; 4, the intracellular programs of the RGCs are activated by inflammatory stimulation, thereby promoting the regeneration of the optic nerve axons; and 5, transplantation of peripheral nerves improves an external inhibition environment, thereby promoting the regeneration of the optic nerve axons. However, since safety of the gene therapy modes such as AAV needs to be verified, due to deficiency of a directional guiding factor, the regenerated axons often fold back during proliferation, thereby affecting the regeneration effect. Due to a drug metabolism problem, the provided exogenous neurotrophic factor or anti-inflammatory and anti-apoptotic drugs have poor performance in promotion of the regeneration of the optic nerve axons. While promoting the regeneration of the axons, the inflammatory stimulation causes endoophthalmitis, thereby easily promoting apoptosis of the RGCs. However, peripheral nerve transplantation materials have limited sources, and rejection easily exists in allograft. Therefore, the above modes are all not transformed to clinical treatment. At present, clinical treatment methods on TON mainly include operations, hormones and combination therapy. The operative treatment is mainly optic canal decompression, i.e., further injuries of bleeding of external and internal vessels of the optic nerves on optic nerve compression are decreased by removing optical canal fracture chips and relieving compression of vessel walls on optic nerves with injuries and edema, so as to increase blood supply of the optic nerves, thereby alleviating swelling of the optic nerves and relative constriction of the optic canal and preventing further deterioration of visual functions so as to restore or partially restore optic nerve tract conduction functions. However, after the optic nerves are injured, an intrinsic apoptotic program will be initiated, and chronic apoptosis of the RGCs cannot be prevented even if inducement of the optic nerve injuries is removed in time by an operation and hormone therapy is combined. Therefore, a novel treatment mode for TON urgently needs to be developed at present.

SUMMARY OF THE INVENTION

To overcome defects in the prior art, the present invention provides a preparation method and an application of a composite scaffold for directionally guiding regeneration of optic nerve axons based on the study of improving an optic nerve injury microenvironment and constructing a tissue engineering scaffold that promotes directional regeneration of the optic nerve axons so as to promote optic nerve regeneration and repair. The prepared directional pipeline composite scaffold has an excellent three-dimensional directional pipeline penetration structure, excellent biocompatibility, excellent biodegradability and appropriate biomechanical property, may be transplanted into an optic nerve injured part, can support the injured optic nerves to avoid degradation or collapse while replacing a local environment after the optic nerve injury, enables the penetration pipeline to facilitate circulation of nutritive materials and guidance of growth of the axons, and has an effect of promoting directional regeneration of the optic nerves.

Technical solutions of the present invention are as follows: the preparation method of the composite scaffold for directionally guiding regeneration of optic nerve axons includes the steps of:

(1) dissolving Type A gelatin ("gelatin A") into deionized water at 70° C. to obtain a gelatin A solution; dissolving sodium alginate into the deionized water at 70° C. to obtain a sodium alginate solution; mixing the two solutions according to a ratio of 1:1; uniformly stirring the mixture; and standing the mixture to remove bubbles;

(2) injecting the mixed solution into a Teflon tubular mold having a diameter of about 12 mm; injecting liquid nitrogen to conduct gradient freezing; stably maintaining an upper temperature of the Teflon tubular mold to be minus 80±20° C.; and maintaining a lower temperature of the Teflon tubular mold to be minus 180±20° C., wherein a temperature difference is 100±20° C.;

(3) refreezing the frozen mixed solution at minus 80±2° C. for 24 hours;

(4) drying the refrozen mixed solution in a freeze drier for 48 hours;

(5) adding a gelatin A and sodium alginate composite scaffold into a genipin solution; and shaking the composite scaffold on a transfer membrane shaker for 24 hours for cross-linking;

(6) closing the transfer membrane shaker after 24 hours; and leave standing for 6 days, thereby obtaining a cross-linkable composite scaffold.

The gelatin A solution obtained in the step (1) has a concentration of 25 mg/ml.

The sodium alginate solution obtained in the step (1) has a concentration of 10 mg/ml.

The genipin solution in the step (5) is a genipin ethanol solution having a concentration of 1 mg/ml, and is preserved in a brown bottle.

The present invention further provides an application of the composite scaffold for directionally guiding regeneration of optic nerve axons in serving as an optic nerve injury repair material.

Beneficial Effects of the Invention

The present invention has beneficial effects as follows: the present invention provides the preparation method and the application of the composite scaffold for directionally guiding regeneration of optic nerve axons. A major component of the composite scaffold is prepared from one or more degradable biomedical materials combined according to different ratios by a gradient freezing method, such as gelatin, sodium alginate, silk fibroin and chitosan, but not limited to the above listed materials. To increase mechanical property of the scaffold or prolong in-vivo degradation time, the scaffold may be cross-linked by a biological cross-linker such as genipin. After gelatin A is added, the prepared composite scaffold has improved excellent mechanical properties and excellent biocompatibility. A problem of solubility differences of the gelatin A produced during gradient freezing can be regulated by sodium alginate, thereby facilitating regular directional pipeline morphology of the scaffold. After cross-linked with genipin, the composite scaffold significantly enhances stability, and the directional pipeline morphology of the scaffold cam provides attachment sites for regeneration of the optic nerve axons, thereby guiding directional regeneration of the optic nerve axons. The composite scaffold provided by the present invention has capacity of guiding the directional regeneration of the optic nerve axons, can be transplanted into an optic nerve injured part to promote the directional regeneration of the optic nerve axons, and serves as an optic nerve injury repair scaffold material.

BRIEF DESCRIPTION OF THE DRAWINGS

FIGS. 4A and 4B is a scanning microscope diagram of a directional pipeline composite scaffold of the present invention, wherein FIG. 4A is a cross section; and FIG. 4B is a longitudinal section;

FIGS. 5A and 5B is a scanning microscope diagram of a scaffold cross-linked with genipin of the present invention, wherein FIG. 5A is a cross section; and FIG. 5B is a longitudinal section;

FIGS. 8A and 8B is an immunofluorescence map within 3 weeks after scaffold transplantation, wherein FIG. 8A is an immunofluorescence map within three weeks after scaffold transplantation in the present invention; a red arrow points to a transplanted scaffold; a white arrow points to optic nerves of a newly grown scaffold; and FIG. 8B is an immunofluorescence map of injured optic nerves that are taken out after an optic nerve injury model is injured;

DETAILED DESCRIPTION OF THE INVENTION

Unless otherwise specified, technical solutions in the present invention are all conventional solutions in the art. Unless otherwise specified, reagents or materials are commercially available.

The present invention may be well described below in combination with drawings and specific embodiments.

The present invention is composed of gelatin A and sodium alginate, wherein a mass ratio of the gelatin A to sodium alginate is 5:2; the gelatin A has a particle model of V900863 and a brand of Sigma-Aldrich; and the sodium alginate has a powder model of S817374 and a brand of Macklin.

Preparation Method:

A composite scaffold capable of guiding regeneration of optic nerves is prepared by mixing gelatin A particles and sodium alginate powder by a gradient freezing method, and then cross-linked with genipin. Specific steps are as follows:

(1) gelatin A was dissolved into deionized water at 70° C., wherein a concentration was 50 mg/ml;

(2) sodium alginate was dissolved into the deionized water at 70° C., wherein a concentration was 20 mg/ml;

(3) the two solutions were mixed according to a ratio of 1:1; the mixture was uniformly stirred; and the mixture was stood to remove bubbles;

(4) the mixed solution was injected into a Teflon tubular mold having a diameter of about 12 mm; liquid nitrogen was injected by a special freezing device to conduct gradient freezing, wherein, during gradient freezing, the Teflon mold should be stably maintained at an upper temperature of minus 80° C. and a lower temperature of minus 180° C.; a temperature difference was 100° C.; and a composite scaffold obtained by the temperature difference had excellent pipe morphology;

(5) the frozen mixed solution was refrozen at minus 80° C. for 24 hours;

(6) the refrozen mixed solution was dried in a freeze drier for 48 hours;

(7) the prepared gelatin A and sodium alginate composite scaffold was cross-linked with genipin;

(8) the genipin was dissolved into a 90% of ethanol solution having a concentration of 1 mg/ml, and the solution was injected into a brown bottle;

(9) the composite scaffold was put into the brown bottle and shaken on a transfer membrane shaker for 24 hours; and

(10) the transfer membrane shaker was closed after 24 hours; and the composite scaffold stood for 6 days, thereby obtaining a cross-linkable composite scaffold.

Figure 1:
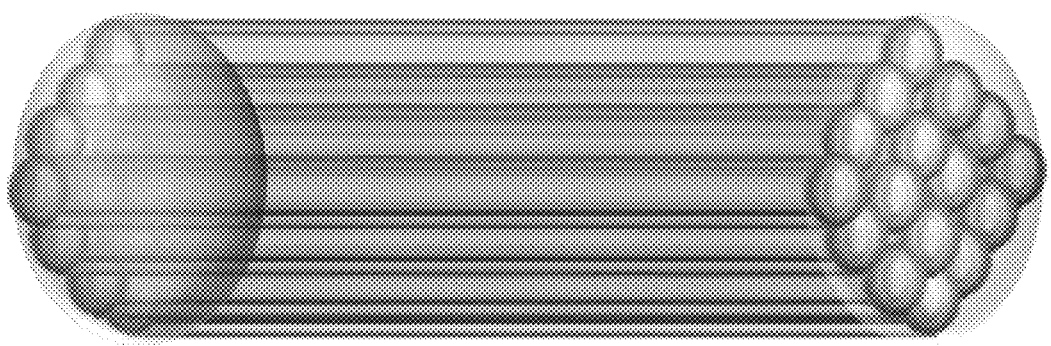
FIG. 1 is a schematic diagram of a synthesized directional pipeline composite scaffold of the present invention.
Figure 2:
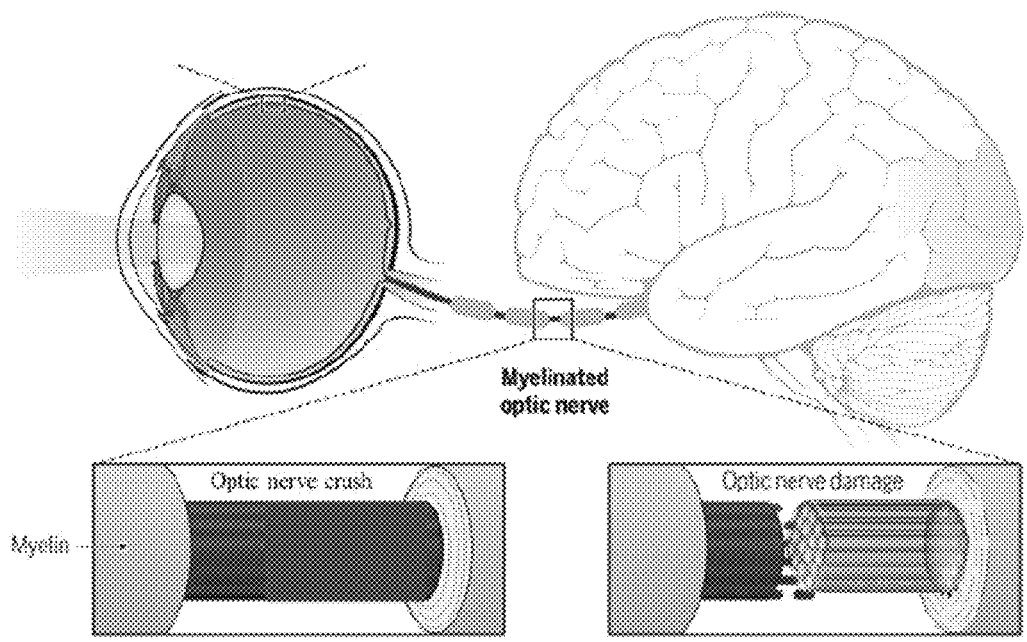
FIG. 2 is a schematic diagram of an application at an optic nerve injured part of the present invention.
Figure 3A:
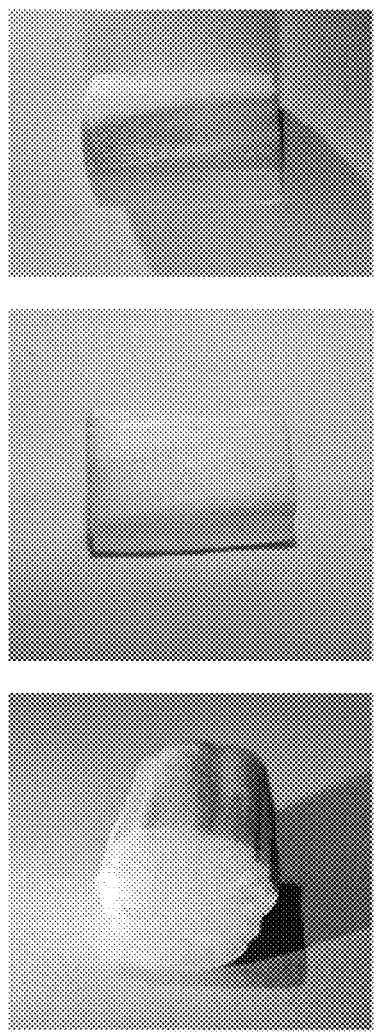
FIGS. 3A and 3B is a naked-eye observation diagram of a composite scaffold before and after cross-linking in the present invention.
Figure 3B:
Figure 3B:
Figure 3B:
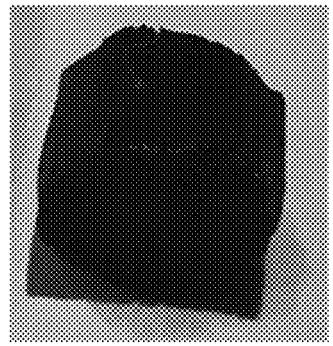
Figure 4A:
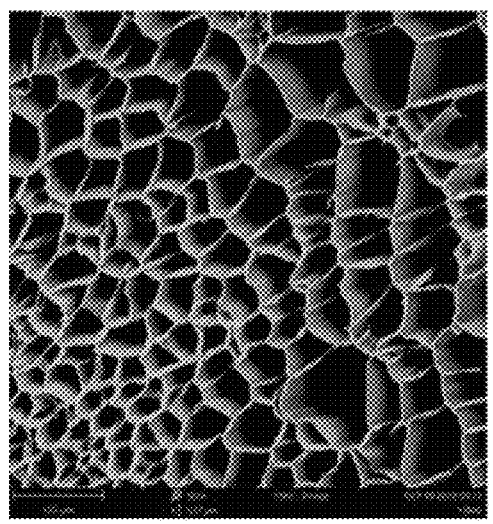
Figure 4B:
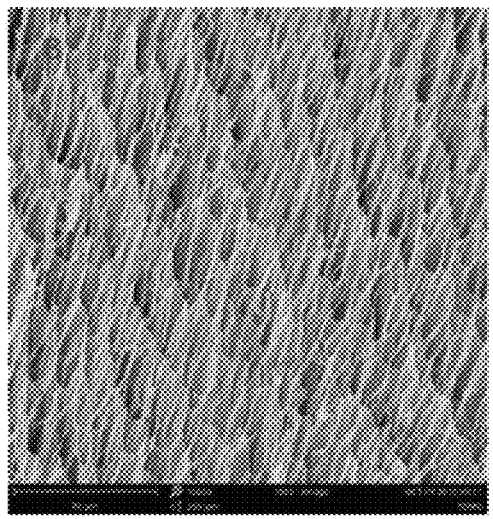
Figure 5A:
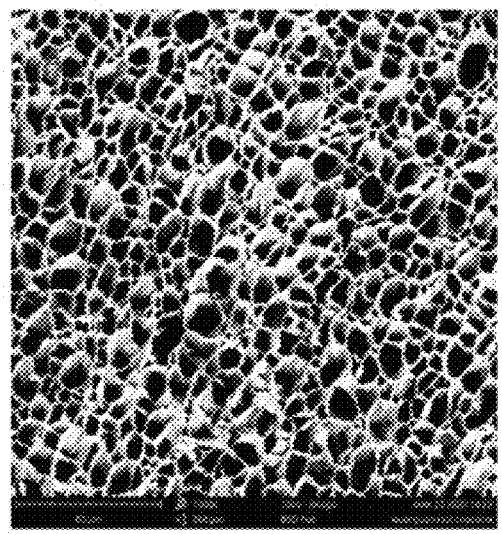
Figure 5B:
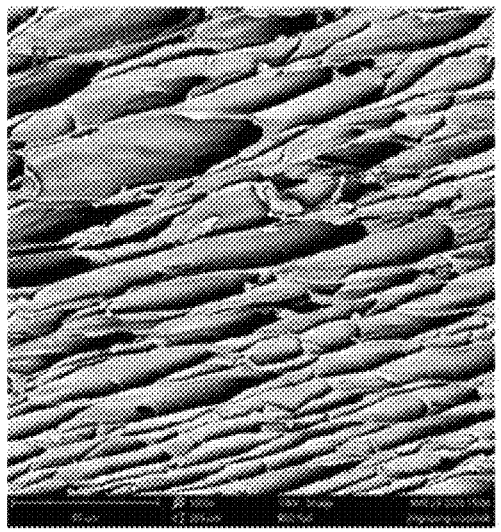

A scanning microscope diagram of the directional pipeline composite scaffold is shown in FIGS. 4A and 4B, wherein FIG. 4A is transverse sections and FIG. 4B is longitudinal sections. Thus, it can be seen that, the composite scaffold has an excellent directional pipeline structure.

The composite scaffold in the present invention is prepared from the gelatin A and sodium alginate, is compounded by the gradient freezing method, has excellent directional pipeline orientation, good biocompatibility, excellent hydrophilcity and protein structure, and is suitable for cell growth and attachment (coming from the composition and structure in Part 3). The gelatin A is produced by partially hydrolyzed with collagens, is a natural protein polymer material, and has excellent biocompatibility. The sodium alginate is a natural polysaccharide extracted from algae, is stable in property and safe and has excellent biocompatibility. Through the gradient freezing mode, directional ice crystals can be produced in the gelatin A and sodium alginate solution and then sublimated by a freeze drier so as to obtain the directional pipeline composite scaffold. The composite scaffold has uniform directional pipelines, has a diameter of about 20 μm, and is suitable for growth of optic nerve axons and circulation of nutritive materials. When a mass ratio of the gelatin A to the sodium alginate is 5:2, the synthesized scaffold has the best pipeline morphology. The genipin is an excellent natural cross-linker, and toxicity of the genipin is far lower than that of glutaraldehyde and any other common chemical cross-linker. When cross-linked with the genipin, it is proved that the composite scaffold has excellent stability and mechanical property and also has excellent biocompatibility.

Figure 6:
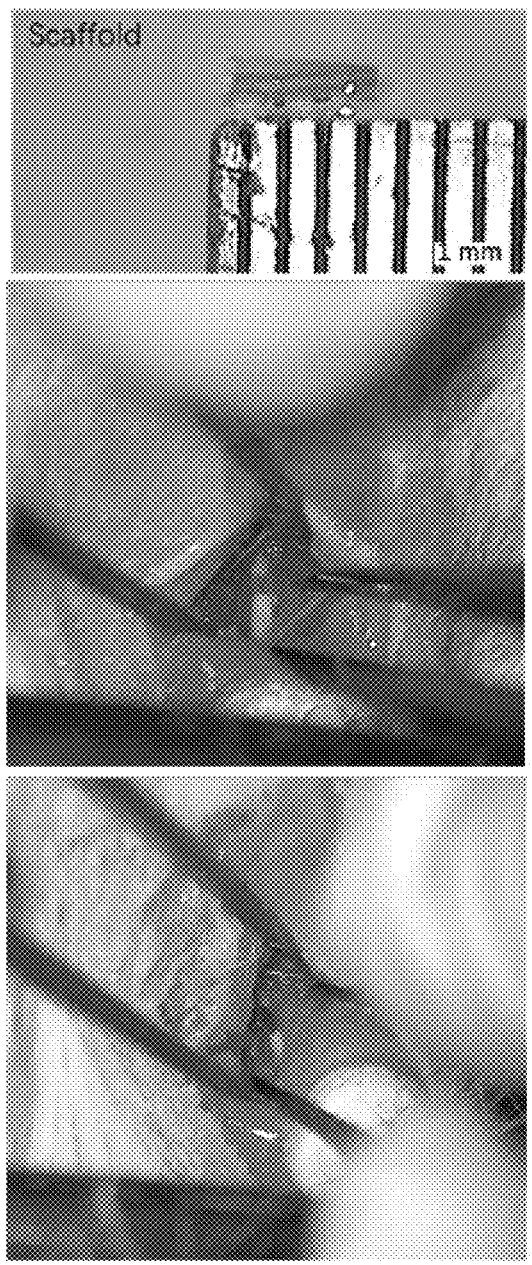
FIG. 6 is a result map of transplantation of an optic nerve scaffold having a length of 2 mm into an optic nerve injury model for rats, wherein a red arrow points to a scaffold transplantation location.

In the present invention, the synthesized directional pipeline composite scaffold was transplanted into an optic nerve injured location to replace an inhibitory microenvironment at the optic nerve injured location, thereby facilitating directional regeneration of optic nerve axons. Animal experiment results are shown as FIG. 6; and an optic nerve scaffold having a length of 2 mm was transplanted into an optic nerve injury model for rats. A red arrow points to a scaffold transplantation location.

Figure 7:
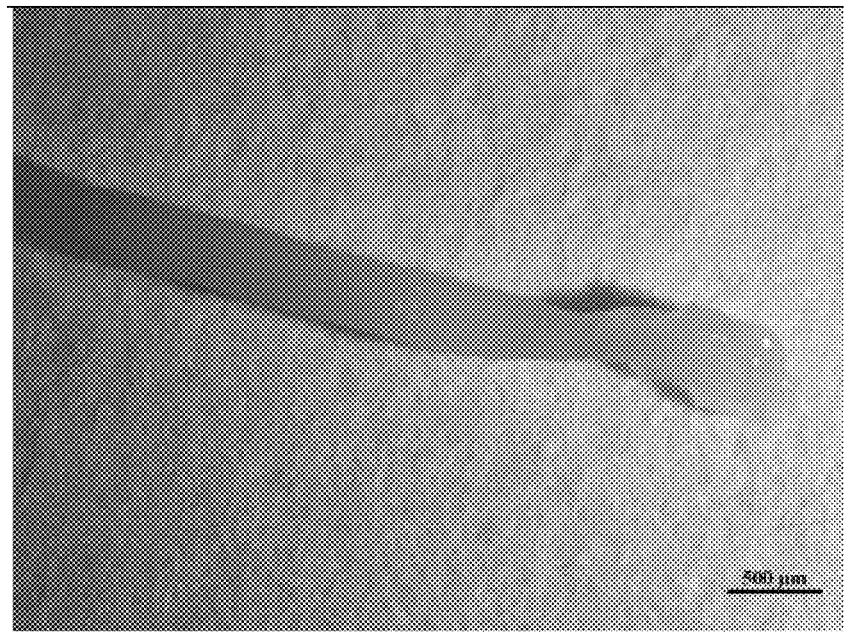
FIG. 7 is a schematic diagram of optic nerves of rats that are taken out within 3 weeks after scaffold transplantation.

Optic nerves of the rats were taken out within 3 weeks after scaffold transplantation; results are shown as FIG. 7; the transplanted scaffold was degraded at the optic nerve injured location; and new axons were grown and filled.

Figure 8A:
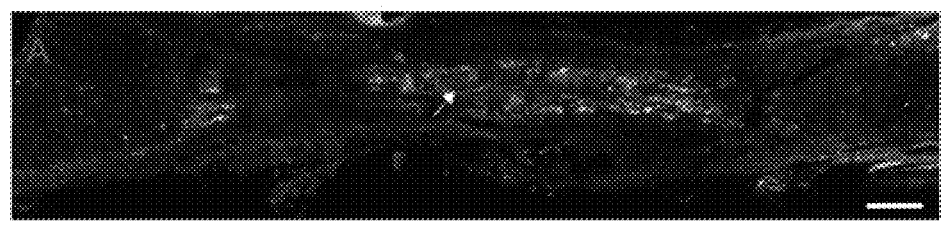
Figure 8B:

Immunofluorescence assay was conducted within 3 weeks after scaffold transplantation; results are shown as FIGS. 8A and B; FIG. 8A was an immunofluorescence map within three weeks after transplantation of the scaffold in the present invention; and a red arrow points to a transplanted scaffold; a white arrow points to optic nerves of the newly grown scaffold. Thus, it can be seen that the scaffold transplantation facilitates regeneration of the optic nerve axons. FIG. 8B is an immunofluorescence map of injured optic nerves that were taken out after the optic nerve injury model was injured, which indicated that no optic nerves were regenerated at the injured location. A scale is 150 μm.

Reference Example 1

Figure 9:
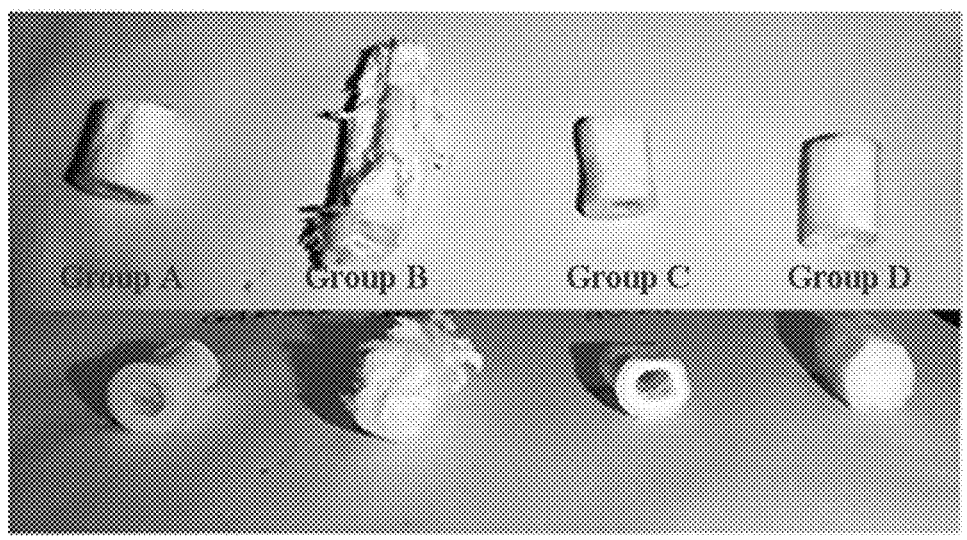
FIG. 9 is a schematic diagram of the macroscopic structure of a composite scaffold synthesized according to different raw material ratios of the present invention.
Figure 10:
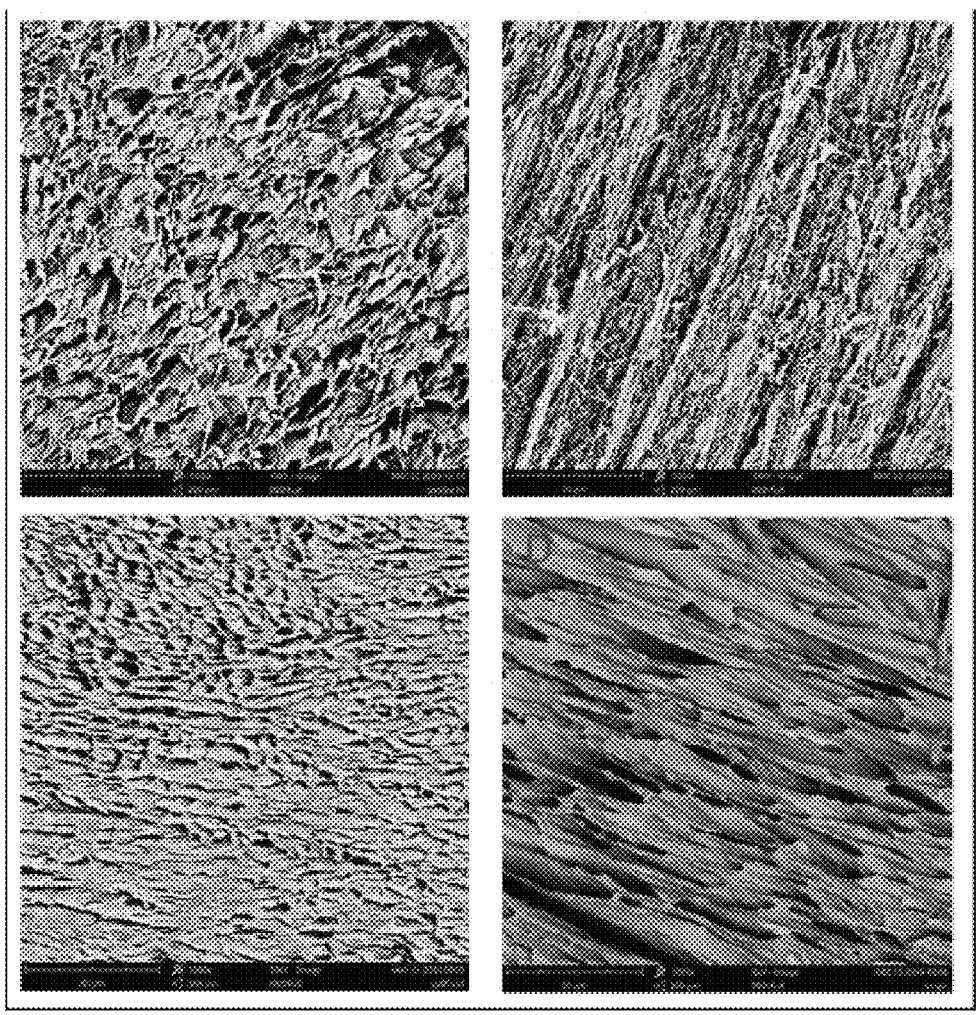
FIG. 10 is a morphology chart of the composite scaffold synthesized according to different raw material ratios of the present invention.

In the present invention, a composite scaffold was synthesized according to different raw material ratios; and a group having the best directional pipeline morphology was selected as the raw material ratio. Results are shown as FIGS. 9 and 10. The groups included a group A (50 mg/ml of gelatin A and 10 mg/ml of sodium alginate), group B (25 mg/ml of gelatin A and 1 mg/ml of sodium alginate), group C (50 mg/ml of gelatin A and 1 mg/ml of sodium alginate) and group D (25 mg/ml of gelatin A and 10 mg/ml of sodium alginate). Bar=80 μm. The group D was selected as the raw material ratio of the directional pipeline composite scaffold.

Reference Example 2

Figure 11:
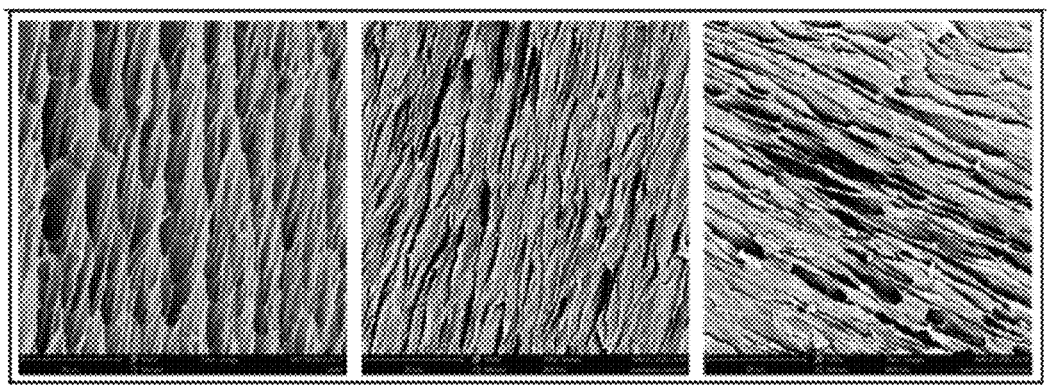
FIG. 11 is a morphology chart of a composite scaffold cross-linked according to different cross-linking manners of the present invention.
Figure 12:
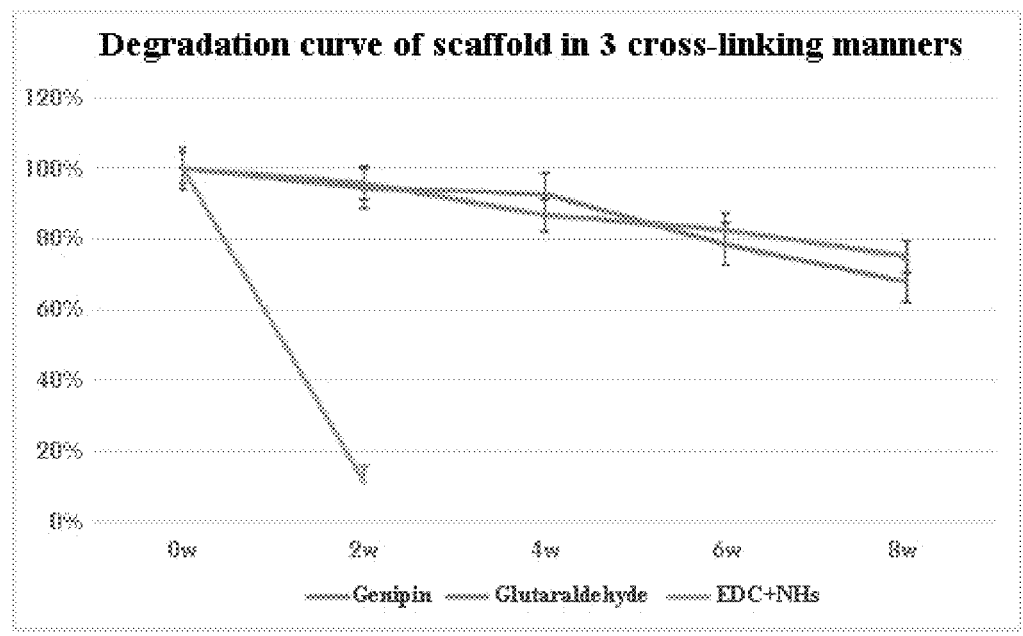
FIG. 12 is a porosity and degradation curve chart of a composite scaffold cross-linked according to different cross-linking manners of the present invention.

In the present invention, results of morphology, porosity and degradation curve of a composite scaffold cross-linked in different cross-linking manners are shown as FIGS. 11 and 12, wherein A, B and C were respectively SEM of the scaffold cross-linked in three manners, such as the genipin, EDC+NHs and glutaraldehyde; and the porosity was about 94.1%. The directional pipeline morphology was the best due to genipin cross-linking; and meanwhile, an expansion rate of the genipin cross-linking was up to 31.3%±10.6%, thereby avoiding occurrence of greater water expanding after the scaffold was transplanted into optic nerves so as not to cause compression to the optic nerves. In a degradation experiment, both the genipin and glutaraldehyde showed excellent stability. Therefore, the genipin is finally selected as the cross-linking manner of the scaffold.

In the present invention, based on thoughts of improving the optic nerve injury microenvironment, controlling adverse factors of axon regeneration and constructing a channel that can guide directional growth of axons, the prepared directional pipeline composite scaffold has a three-dimensional directional pipeline penetration structure, excellent biocompatibility and appropriate biomechanical properties, can support the injured optic nerves to avoid degradation or collapse while replacing an injured optic nerve inhibition environment, enables the penetration pipeline to facilitate circulation of nutritive materials and growth of the axons, and has an effect of guiding directional regeneration of the optic nerves. The gelatin A and sodium alginate composite scaffold prepared in the embodiments has excellent biocompatibility, a certain mechanical property and in-vivo stability, and can simultaneously provide regeneration and attachment media for the optic nerve axons and guide directional growth of the axons. Therefore, the composite scaffold is regarded as an optic nerve repair scaffold material of great potential.

The above descriptions are merely preferred embodiments of the present invention. The protection scope of the present invention is not limited to the above embodiments only. All technical solutions belonging to the thought of the present invention shall fall within the protection scope of the present invention. It should be indicated that, several improvements and modifications made by those ordinary skilled in the art without departing from the principles of the present invention shall be regarded as the protection scope of the present invention.

The invention claimed is:

1. A method of preparing a composite scaffold for directionally guiding regeneration of optic nerve axons comprising the steps of:
   (1) dissolving a Type A gelatin into deionized water to obtain a gelatin A solution; dissolving sodium alginate into the deionized water to obtain a sodium alginate solution; mixing the two solutions according to a ratio of 1:1; uniformly stirring the mixture; and allowing the mixture to stand to remove bubbles;
   (2) injecting the mixed solution into a polytetrafluoroethylene tubular mold; injecting liquid nitrogen into the polytetrafluoroethylene tubular mold to conduct gradient freezing; stably maintaining an upper temperature of the polytetrafluoroethylene mold to be minus 80±20° C.; and maintaining a lower temperature of the polytetrafluoroethylene mold to be minus 180±20° C., wherein a temperature difference is 100±20° C.;
   (3) refreezing the frozen mixed solution at minus 80±2° C.;
   (4) drying the refrozen mixed solution in a freeze drier;
   (5) adding a Type A gelatin and sodium alginate composite scaffold into a genipin solution; and shaking the composite scaffold on a transfer membrane shaker for cross-linking; and
   (6) closing the transfer membrane shaker after completion and allowing the composite scaffold to stand; thereby obtaining a cross-linked composite scaffold.

2. The method of preparing a composite scaffold for directionally guiding regeneration of optic nerve axons according to claim 1, wherein the gelatin A solution obtained in the step (1) has a concentration of 25 mg/ml.

3. The method of preparing a composite scaffold for directionally guiding regeneration of optic nerve axons according to claim 1, wherein the sodium alginate solution obtained in the step (1) has a concentration of 10 mg/ml.

4. The method of preparing a composite scaffold for directionally guiding regeneration of optic nerve axons according to claim 1, wherein the genipin solution in the step (5) is a genipin ethanol solution having a concentration of 1 mg/ml.

5. A composite scaffold prepared by the method according to claim 1.

* * * * *